United States Patent [19]
Gayer et al.

[11] Patent Number: 6,094,467
[45] Date of Patent: Jul. 25, 2000

[54] METHOD FOR IMPROVING CT IMAGES HAVING HIGH ATTENUATION OBJECTS

[75] Inventors: Arie Gayer, Mizkeret-Batya; Ehud Nachaliel, Lower Galilee, both of Israel

[73] Assignee: Marconi Medical Systems Israel Ltd., Haifa, Israel

[21] Appl. No.: 09/150,246

[22] Filed: Sep. 10, 1998

[30] Foreign Application Priority Data

Sep. 15, 1997 [IL] Israel ......................................... 121773

[51] Int. Cl.$^7$ ...................................................... A61B 6/03
[52] U.S. Cl. .................... 378/4; 378/8; 378/901
[58] Field of Search .............. 378/4, 8, 15, 901

[56] References Cited

U.S. PATENT DOCUMENTS

| | | |
|---|---|---|
| 4,217,641 | 8/1980 | Naparstek . |
| 4,245,244 | 1/1981 | Lijewski et al. . |
| 4,590,558 | 5/1986 | Glover et al. . |
| 4,616,318 | 10/1986 | Crawford ................................. 378/54 |
| 4,624,007 | 11/1986 | Muranushi . |
| 4,709,333 | 11/1987 | Crawford . |
| 4,792,900 | 12/1988 | Sones et al. . |
| 5,243,664 | 9/1993 | Tuy . |
| 5,933,471 | 8/1999 | Kalvin ......................................... 378/4 |

*Primary Examiner*—David V. Bruce
*Attorney, Agent, or Firm*—Fenster & Company Patent Attorneys, Ltd.

[57] ABSTRACT

A method is provided for improving visual definition in a CT X-ray image having high attenuation objects such as metal prostheses and implants. The method provides for determining extents of the high attenuation objects and reducing the artifacts that the high attenuation objects cause in the image without completely removing the high attenuation objects from the image.

31 Claims, 6 Drawing Sheets

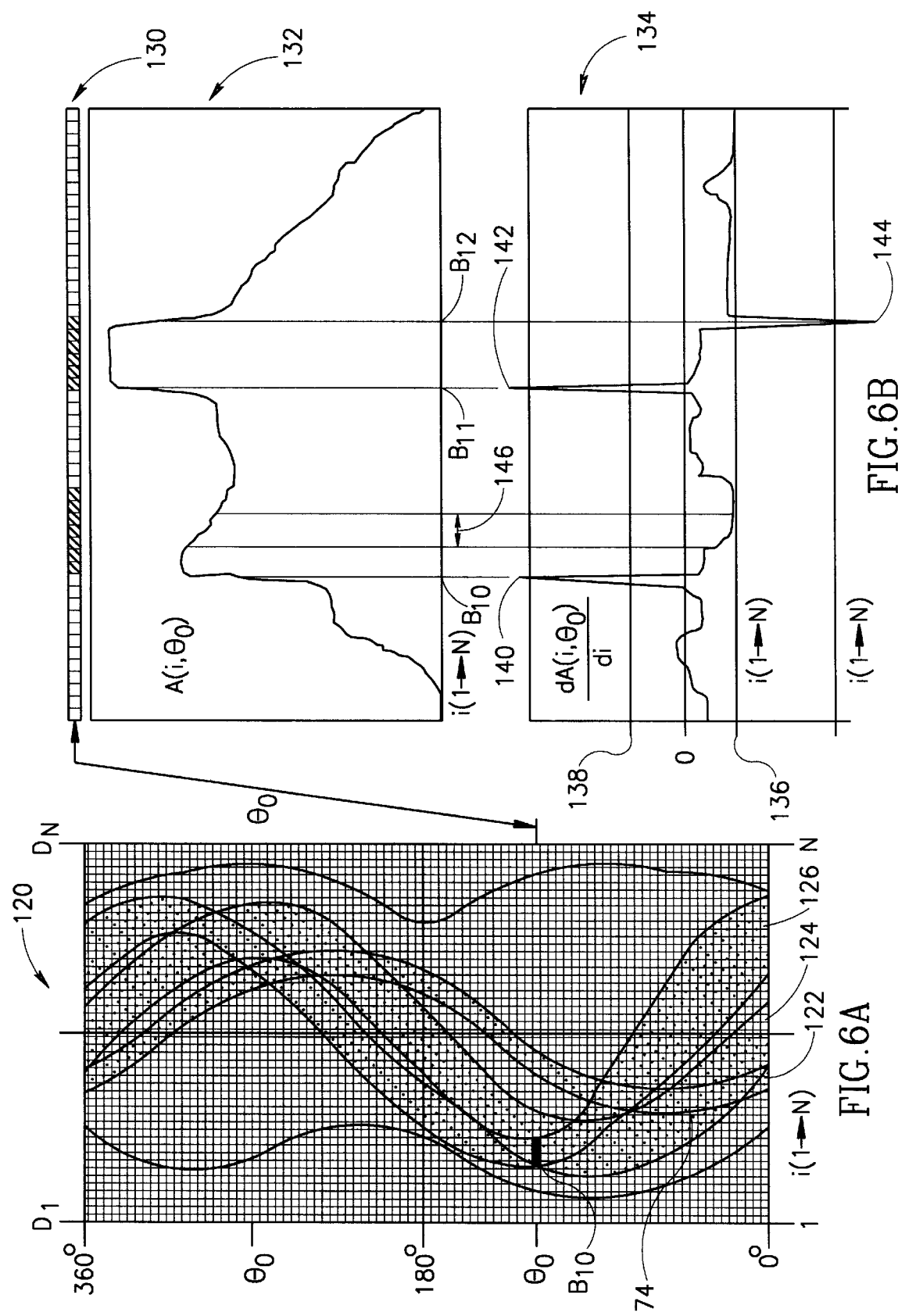

METHOD FOR IMPROVING CT IMAGES HAVING HIGH ATTENUATION OBJECTS

FIELD OF THE INVENTION

The present invention relates to CT X-ray imaging, and in particular to improving visual definition in CT images containing high attenuation objects, and in particular metal inserts in medical CT images, which are present in an imaged subject, and to reducing the intensity of artifacts that the objects and inserts cause.

BACKGROUND OF THE INVENTION

In CT X-ray imaging, a slice of a subject is imaged by irradiating it with X-rays in an X-ray beam emanating from an X-ray source in the plane of the slice. X-rays are incident on the slice along an edge of the slice which faces the X-ray source and pass through material in the slice. The material in the slice attenuates the beam by absorbing and scattering X-rays. The slice thus shadows the beam and the amount by which the beam is attenuated is a function of the amount and composition of the material in the slice and the energy spectrum of the X-ray beam.

Downstream of the slice, X-rays not absorbed or scattered, are detected by small aperture X-ray detectors, closely packed side by side, along an arc or in a complete circle, in the plane of the slice and oriented facing the X-ray source. Each detector measures the intensity of X-rays that have reached it after traversing a narrow tubule of material in the slice that lies along the line projected from the X-ray source to the detector. Each detector thus measures the attenuation of the beam resulting from the composition and density of all the material in the tubule. The cross sectional area of the tubule is substantially equal in size and shape to the size and shape of the X-ray beam spot on the aperture of the X-ray detector.

If $I_0$ is the intensity of X-rays that enter a tubule at its upstream end and I is the intensity of the X-rays exiting the tubule at its downstream end, then $I=I_0 \exp(-\int \mu(l)dl)$ (ignoring dependence of absorption on X-ray energy), where the integral is taken over the length of the tubule, and $\mu(l)$ is the absorption coefficient per centimeter for X-rays, in the material of the tubule at point l along the tubule. Since $I_0$ is known and I is measured by a detector then $\ln(-I/I_0)=\int \mu(l)dl$ and the X-ray intensity measurement at the detector is in effect a measurement of $\int \mu(l)dl$, hereafter an "attenuation measurement", for a tubule of material in the slice.

In medical CT imaging, the absorption coefficient $\mu$ of a material is commonly measured in CT units which is the absorption coefficient of the material relative to the absorption coefficient of pure water which is assigned a CT number equal to 0. Soft tissues commonly have CT numbers in the range from –1000 to 500, bone CT number is about 800, and metals often have CT numbers in excess of 2000.

A subfan angle is defined as the angle of the position of the X-ray source around the slice, measured from some convenient base line in the plane of the slice, from which the slice is irradiated. For a given subfan angle attenuation measurements are made for a large number of closely packed non overlapping tubules through the slice. The tubules are essentially contiguous and their number is large enough so that, at the given subfan angle, almost all points in the slice fall within a tubule and attenuation measurements are made for substantially the whole volume of the slice. The angle that a particular tubule makes with the base line when an attenuation measurement is made is called a view angle of the tubule. Each attenuation measurement is therefore identified by a view angle, and the particular tubule at the view angle, for which the attenuation measurement is made.

It is convenient to label the tubules with an index number that identifies the detector in the detector array which measures the X-rays transmitted through the tubule. Let the detectors in the detector array in the plane of the slice be labeled by consecutive increasing integers $i=1,2, \ldots N$ according to increasing displacement from detector "1". Then if the view angle is $\theta$, the attenuation measurements can be written as a function of i and $\theta$, in the form $A(i,\theta)$.

A set of attenuation measurements $A(i,\theta)$, is generally acquired for N tubules at each of many closely spaced subfan angles around a slice, from 0 to 180 degrees or from 0 to 360 degrees. Before reconstruction into an image, the acquired data from all the subfan angles is generally rebinned and organized into sets of data comprising N attenuation measurements for parallel tubules at a same view angle. The set of N measurements at a particular view angle is called a view. The set of views for all view angles around the slice at which data was acquired is called a projection set for the slice. From the projection set a map of the X-ray absorption coefficient of the material in the slice as a function of position in the slice can be determined. This map shows different structural features inside the slice. By mapping the absorption coefficient in this way for many slices, a three dimensional picture of the internal structures of the subject can be constructed.

There are a number of different algorithms and many different variations of algorithms that are used for processing attenuation data to construct a CT image of a slice irradiated by X-rays. A problem that continuously arises with image construction algorithms commonly used for medical CT imaging, is that objects that have sharply defined boundaries and high CT numbers compared to the CT numbers of surrounding body tissues are poorly imaged and give rise to artifacts in the constructed CT image. These artifacts distort and degrade the image. Examples of such objects are surgical clips, metal prosthesis and implants, dental fillings, or metal objects that have penetrated the body as a result of accident or violence, hereafter "metal inserts". Metal inserts typically give rise to artifacts called starbursts which comprise patterns of bright and dark bands emanating from the dense object. The artifacts typically comprise streaks across the constructed CT image which degrade and obliterate detail. As a result of such artifacts, important information, such as whether a bullet is touching the spinal column or a major artery, or how much clearance there is between an implant and a vital organ, cannot be accurately assessed.

Procedures have been developed to ameliorate these artifact effects by replacing or modifying attenuation data for tubules that pass through a metal insert in an imaged slice. Many of these procedures define "rub out" regions in the projection set data for the slice. Data from tubules passing through the rub out regions is discarded and replaced with data interpolated from attenuation data from tubules outside of and adjacent to both sides of the rub out regions. This "rub-out" of data, in effect, throws away the data from the offending metal insert and removes the metal insert from the constructed CT image. While this improves the image, information about the metal insert is discarded, and the relation of the metal insert to structures and tissues in the body, that is often important, is not imaged.

U.S. Pat. No. 4,590,558, to Gary H. Glover et al describes removing artifacts from a CT image of a subject which artifacts are caused by a high density object present in the subject. As described in this patent, in order to remove or reduce the artifacts, data from the high density object is removed from a rubout region of the projection set of the subject. This, in effect, removes or reduces the artifacts in the image caused by the object, by removing the object.

U.S. Pat. No. 4,709,333, to Carl R. Crawford, describes a similar approach for the case where two high density objects are present in an imaged subject. In this patent a method is presented for removing data resulting from the two high density objects at regions of a projection set of the subject where the two objects shadow each other. As in the above patent artifacts are removed by removing the objects causing them.

Other techniques use iterative methods to correct CT images for the presence of artifacts resulting from metal inserts present in an imaged slice. Some of these techniques do not delete the metal insert from the constructed CT image of the slice but they are generally computationally complicated and often require many iterative steps. Such an iterative method is disclosed in U.S. Pat. No. 5,243,664 to Heang K. Tuy.

It would be desirable to have a computationally inexpensive algorithm that reduces artifacts in a CT image of a slice of a subject that are caused by metal inserts present in the slice, without removing the metal inserts from the image.

SUMMARY OF THE INVENTION

It is an object of the present invention to provide a computationally inexpensive method for improving CT imaging of metal inserts present in biological tissue and for reducing artifacts from such objects that degrade CT images of the biological tissue.

It is an object of one aspect of the present invention to provide a procedure for accurately identifying attenuation measurements in a view that are affected by a metal insert.

It is an object of another aspect of the present invention to provide a procedure for adjusting the attenuation measurements so identified to improve imaging of the metal insert and to reduce artifacts it causes in the constructed image in which it appears.

A further object of another aspect of the present invention is to provide a set of constraints that limit the results obtained from the application of procedures provided by other aspects of the invention so that these results fall within acceptable ranges. If a result is outside a range set by a constraint it is, preferably, discarded and replaced by a result obtained, preferably, from interpolation of appropriate data from views adjacent to the view for which data is being adjusted.

It has been found by the present inventors that for metal inserts, the magnitude of the derivative of the attenuation $A(i,\theta)$ with respect to tubule position i, is a better indicator of the boundaries of metal inserts in CT views than is the magnitude of the attenuation. Therefore, in a preferred embodiment of the present invention, the boundaries of a metal insert in a view, at view angle $\theta_0$, are marked by the points i at which the absolute value of the derivative of $A(i,\theta_0)$ with respect to i has a peak which exceeds a predetermined threshold. The boundaries of the metal insert are preferably located by pairs of peaks, one of which is positive and one of which is negative. If these points are labeled $i_1$ and $i_2$, ($i_1<i_2$, with $dA(i_1,\theta_0)/di>0$ and $dA(i_2,\theta_0)/di<0$) then the metal object extends from $i_1$ to $i_2$ in the view and all values of $A(i,\theta_0)$ for which $i_1<i<i_2$ are considered to be affected by the metal insert and to require adjustment.

In a preferred embodiment of the present invention constraints are applied which limit the widths of peaks which are used to identify metal insert boundaries. In some complicated images the exact value of i which is chosen as the position of a peak can be affected by the width of the peak. For broad peaks it is sometimes difficult to accurately identify a particular value of i which is the position of the peak. In such cases constraints on width can be particularly useful.

Physically, the metal object in the imaged tissue lies between the tubules labeled by $i_1$ and $i_2$ and these tubules pass through opposite edges of the metal object in the plane of the slice at view angle $\theta_0$. Tubules at view angle $\theta_0$, for which $i_1<i<i_2$, pass through the metal insert, and attenuation measurements for these tubules are severely affected by the metal insert. Tubules for which $i<i_1$ or $i_2<i$, do not pass through the metal insert. As a result attenuation measurements for tubules for which $i<i_1$ or $i_2<i$, are not affected by the metal insert.

In some preferred embodiments of the present invention, alternatively or additionally, the second derivative of $A(i,\theta_0)$ is used in locating boundaries of metal inserts. At a metal insert boundary, the second derivative of $A(i,\theta_0)$ has a very specific signature, exhibiting a sharp positive peak followed closely by a sharp negative peak. The cross over point between the two peaks, where the second derivative is zero, is a good indicator of the position of the metal insert boundary.

In preferred embodiments of the present invention, contributions to the magnitudes of attenuation measurements affected by a metal insert are not completely removed. Instead, they are moderated so as to reduce artifacts they cause in a CT image but to still have sufficient effect on the attenuation data so that the metal insert can be clearly visualized in the image.

In preferred embodiments of the present invention, once attenuation measurements affected by a metal insert present in a slice of an object imaged are identified, contributions to the magnitude of the measurements that arise from the metal insert are estimated. These contributions are estimated as the differences between the values of the affected measurements and values for the affected measurements that are estimated that would be measured in the absence of the metal insert. Values for the affected measurements in the absence of the metal insert are preferably calculated by linear interpolation from attenuation measurements $A(i,\theta)$ at opposite boundaries just outside of the extent of the metal object in the view (i.e. near to $i_1$ and $i_2$ and just outside of the region $i_1 \rightarrow i_2$), although other methods known in the art may be used.

Each of the affected attenuation measurements is adjusted by subtracting from it, a large proportion of the estimated contribution to its value arising from the metal insert. The proportion subtracted preferably depends upon the material of the metal insert and the CT number of the material.

For most metals the proportion subtracted is preferably greater than 0.5. For metal inserts made from iron, the proportion is preferably greater than 0.7. Preferably, the proportion subtracted is in the range from 0.7 to 0.8. Most preferably the proportion subtracted is substantially equal to 0.75.

For metal inserts made from heavier metals such as mercury, gold or platinum, preferably the proportion subtracted is greater than 0.8. More preferably, the proportion subtracted is greater than 0.9. Most preferably, the proportion subtracted is in the range from 0.93 to 0.99. Preferably the proportion subtracted is substantially equal to 0.95.

Values for the proportion subtracted that are less than 0.5 can also improve the quality of an image with a metal insert. Generally, as the proportion subtracted increases, artifacts caused by a metal insert fade and the edges of the insert and the position of the insert with respect to nearby body tissue are more clearly imaged. The intensity with which the metal insert is imaged also decreases. At some value for the proportion subtracted, an optimum balance is achieved between the artifacts and the intensity with which the metal insert is imaged. Increases in the proportion subtracted beyond this value decrease the intensity of the image of the metal insert without necessarily providing imaging benefits resulting from further reduction in the intensity of the artifacts.

Where adjustments to data in accordance with a preferred embodiment of the present invention are performed automatically by computer it is possible to change the proportion subtracted and observe how the changes affect the CT image constructed from the adjusted data. In this way it is possible to visually optimize the proportion subtracted.

In preferred embodiments of the present invention, the procedures for identifying and moderating attenuation measurements are preferably applied to all the views of a projection set of a slice imaged. This results in a moderated projection set which when processed, preferably by filtered back projection, produces a clear well defined image of the metal insert and the tissue region in which it is situated.

Practically, clinical CT images can be very complicated. At some view angles in a CT scan an insert or prosthesis or other high CT number object may be shadowed by dense biological tissue such as bone, or there may be more than one insert, prosthesis or other high CT number object present in a patient which shadow dense biological tissue and each other simultaneously at various view angles. In addition, several medium CT number objects, such as bones or parts of a bed on which a patient who is being scanned is lying, can simulate metal objects under certain conditions and in certain views. For these problematic view angles, the shadowing can distort the boundaries of metal inserts, and adjustments to the attenuation data of the projection set at these view angles, performed as described above, are potentially unreliable. For such situations methods for adjusting data of a projection set, in accordance with a preferred embodiment of the present invention, invoke a set of constraints comprising at least one constraint, which when constraints in the set of constraints are are not satisfied, modify the way the adjustments are made.

The constraints are preferably based on the requirement that the attenuation data be consistent for all view angles of a projection set. The constraints preferably require: the width of a metal insert in any view should not exceed two standard deviations of the width of the metal insert averaged over all the views; from view to view the sum of the widths of all metal inserts should change smoothly; the assessed contribution to attenuation measurements from a metal insert should be within two standard deviations of the average of the assessed contribution it makes taken over all views of the projection set.

For any view where these constraints are not met adjustments to attenuation measurements affected by a metal insert are preferably made by estimating the boundaries of metal inserts and/or metal insert attenuation by interpolation from data at adjacent or nearby view angles at which the constraints are met.

Procedures provided by various aspects of the present invention are generally applicable to projection set data independent of the generation of CT scanner used to acquire the projection set data and they are computationally inexpensive and readily computerized. Preferably, these procedures are performed automatically as part of a computerized algorithm for processing projection set data.

There is therefore provided in accordance with a preferred embodiment of the present invention a method for locating boundaries of metal inserts in an array of attenuation data of a set of CT X-ray attenuation data comprising a plurality of arrays of attenuation data, wherein each array of attenuation data represents attenuation data acquired for a plurality of substantially contiguous paths through a slice of a subject, comprising: (a) evaluating the derivative of the attenuation data with respect to a position coordinate of the array of attenuation data; (b) setting a derivative threshold; (c) identifying positive and negative boundary peaks as positive and negative peaks in the derivative respectively that have an absolute value greater than the derivative threshold; (d) determining the positions of the positive and negative boundary peaks; and (e) determining the position of boundaries of metal inserts in the array of attenuation data to be positions of positive and negative boundary peaks.

Preferably determining the positions of positive and negative boundary peaks comprises: (a) evaluating the second derivative of the attenuation data with respect to the position coordinate of the array of attenuation data; (b) setting a second derivative threshold; (c) setting a second derivative maximum width; (c) identifying positive second derivative peak pairs as a positive peak in the second derivative followed by a negative peak, wherein the separation of the positions of the two peaks is less than the second derivative maximum width and wherein the magnitude of both peaks is greater than the second derivative threshold; (d) identifying negative second derivative peak pairs as a negative peak in the second derivative followed by a positive peak, wherein the separation of the positions of the two peaks is less than the second derivative maximum width and wherein the magnitude of both peaks is greater than the second derivative threshold; (e) determining the position of each positive and negative second derivative peak pair as the position of the point between the two peaks at which the second derivative is zero; and (f) determining the positions of positive boundary peaks as the positions of positive second derivative peak pairs and the positions of negative boundary peaks as the positions of negative second derivative peak pairs.

There is also provided a method for determining the extent of each of at least one metal insert in an array of attenuation data of CT attenuation data comprising: (a) defining boundary peak pairs, wherein a boundary peak pair comprises a positive boundary peak and a negative boundary peak chosen from the identified boundary peaks and wherein the positive boundary peak has a value for the position coordinate which is less than the value for the position coordinate of the negative boundary peak; and (b) determining the extent of each of the at least one metal insert in the array of attenuation data to be a region between the positions of the boundary peaks in a boundary peak pair.

Preferably, defining boundary peak pairs comprises: (a) choosing the positive and negative boundary peaks of a boundary peak pair so that there is no negative boundary peak between them; and (b) choosing positive boundary peaks for boundary peak pairs so that, for a positive boundary peak of a boundary peak pair there is no positive boundary peak having a smaller value for the position coordinate that is not a positive boundary peak of a different boundary peak pair or that is not bracketed by the positive and negative boundary peaks of a different boundary peak pair.

Alternatively or additionally defining boundary peak pairs preferably comprises: (a) choosing the positive and negative boundary peaks of a boundary peak pair so that there is no positive boundary peak between them; and (b) choosing negative boundary peaks for boundary peak pairs so that, for a negative boundary peak of a boundary peak pair there is no negative boundary peak having a larger value for the position coordinate that is not a negative boundary peak of a different boundary peak pair or that is not bracketed by the positive and negative boundary peaks of a different boundary peak pair.

Preferably, extents of each of the at least one metal insert satisfy at least one constraint of a constraint set. Preferably, the constraint set comprises a constraint that the absolute difference between the determined extent of each of the at least one metal insert in any array of attenuation data of the set of CT X-ray attenuation data, and its average width, be less than two standard deviations of its average width, where the average width is the width of the insert averaged over all views. The constraint set preferably comprises a constraint that the sum of the determined extents of all of the at least one metal insert, changes smoothly between adjacent arrays of attenuation data of the set of CT X-ray attenuation data.

Preferably, determining the extent of metal inserts of the at least one metal insert in an array of attenuation data where a constraint is not satisfied, by interpolation from data available in arrays of attenuation data adjacent to or near to the array of attenuation data where a constraint is not satisfied.

There is further provided a method for adjusting attenuation data in a set of CT X-ray attenuation data acquired for a slice of a subject having a metal insert comprising: (a) determining the contribution that the metal insert makes to the magnitude of each attenuation datum in the set of CT X-ray attenuation data; and (b) adjusting each attenuation datum by subtracting from it a fraction less than one of the determined contribution to its magnitude arising from the metal insert.

Preferably, a CT number for the metal insert is calculated from the set of CT X-ray attenuation data and the calculated CT number is used to determine the fraction. Preferably, the CT number is calculated by a computer program.

Alternatively, or additionally, there is a priori knowledge about the CT number of the metal insert, and the a priori knowledge is used to determine the fraction.

In some preferred embodiments of the invention, the fraction is determined by adjusting the fraction until a view reconstructed from the set of CT X-ray attenuation data is optimized.

In some preferred embodiments of the invention, the fraction is greater than 0.5. Preferably, the fraction is in the range from 0.7 to 0.8 for metal inserts having a CT number in the region of the CT numbers of iron or titanium. More preferably, the fraction is substantially equal to 0.75.

Preferably, the fraction is greater than 0.8 for metal inserts having a CT number in the region of the CT numbers of mercury, gold or platinum. More preferably, the fraction is 0.95.

Preferably, determining the contribution that the metal insert makes to the magnitude of each attenuation datum in the set of CT X-ray attenuation data, comprises requiring that the contribution to each attenuation datum from the metal insert satisfies at least one constraint in a constraint set. The constraint set preferably comprises a constraint that the sum of the calculated contributions to all attenuation data in an array of attenuation data from a metal insert be constant to within two standard deviations of its average taken over all arrays of attenuation data of the set of CT X-ray attenuation data.

Determining the contribution to an attenuation datum in the set of CT X-ray attenuation data from the metal insert preferably comprises calculating an estimate for the value of the attenuation datum assuming the metal insert is absent, subtracting the estimate from the attenuation datum and setting the contribution to the attenuation datum equal to the results of the subtraction.

Preferably, calculating an estimate for the value of the attenuation datum assuming the metal insert is absent comprises calculating the estimate from data in the array of attenuation data of the set of CT X-ray attenuation data to which the datum belongs that is not affected by the metal insert.

Data in the array of attenuation data of the set of CT X-ray attenuation data to which the datum belongs that is not affected by the metal insert is preferably attenuation data at positions in the array of attenuation data that are adjacent to and outside of the extent of the metal insert in the array of attenuation data.

Preferably, the value of the attenuation datum assuming the metal insert is absent is estimated by linear interpolation between attenuation data or averages of attenuation data at positions in the array of attenuation data that are adjacent to and outside of the extent of the metal insert in the array of attenuation data.

Preferably, determining the contribution that the metal insert makes to the magnitude of each attenuation datum in an array of attenuation data of the set of CT X-ray attenuation data when a constraint of the constraint set is not satisfied comprises iteratively scaling the intercept of the linear interpolation until the constraint is satisfied.

In some preferred embodiments of the invention, a set of CT X-ray attenuation data is a projection set.

In some preferred embodiments of the invention, an array of attenuation data is a view.

BRIEF DESCRIPTION OF FIGURES

The invention will be more clearly understood by reference to the following description of preferred embodiments thereof in conjunction with the figures, wherein identical structures, elements or parts which appear in more than one figure are labeled with the same numeral in all the figures in which they appear, in which:

FIGS. 6A and 6B respectively show a sinogram of simulated attenuation data for the slice shown in FIG. 5 and details of the data and processed data for a view angle shown in FIG. 5 at which the bone tissue is shadowed by the part of the bed.

DETAILED DESCRIPTION OF PREFERRED EMBODIMENTS

Figure 1:
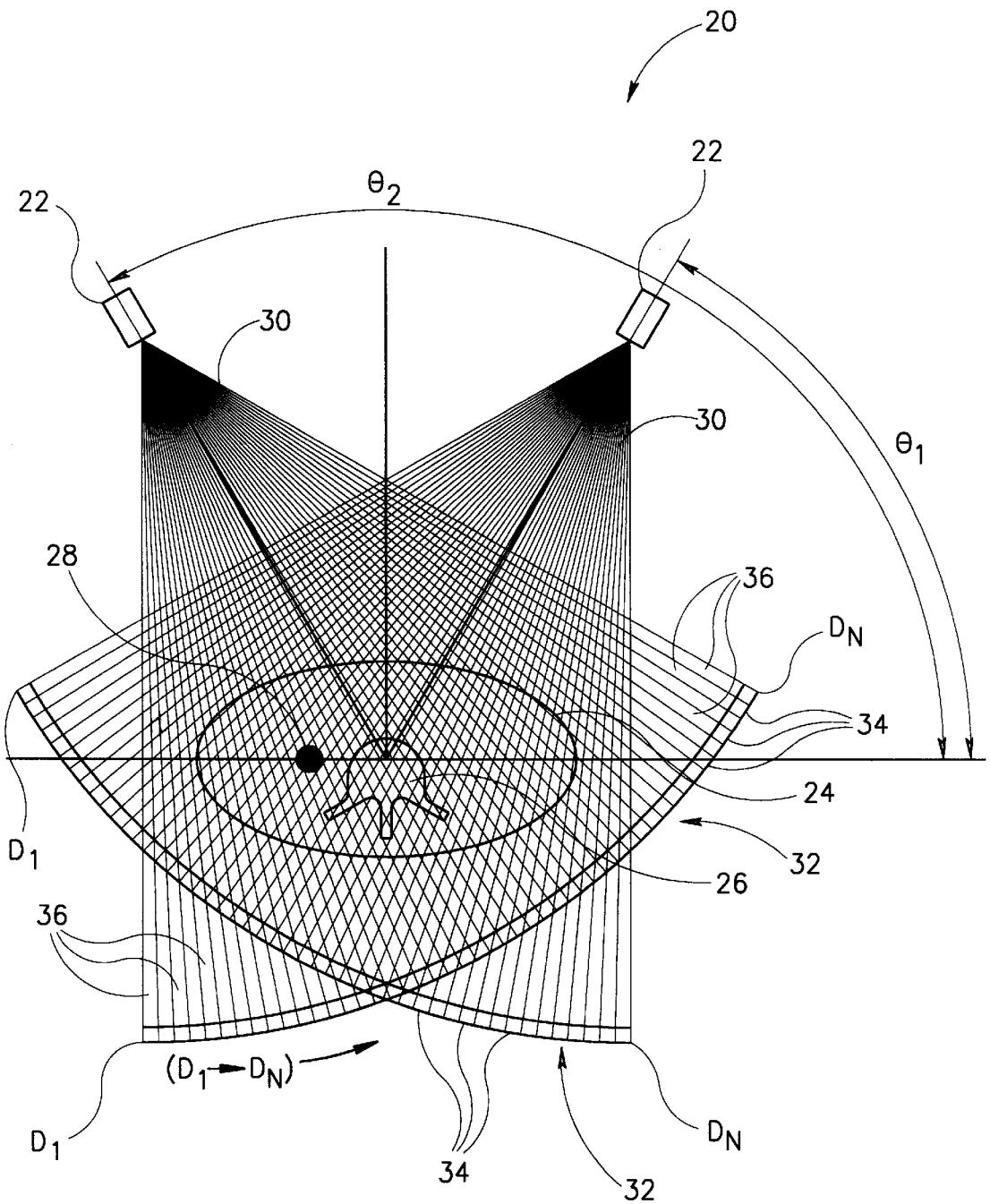
FIG. 1 shows a schematic diagram of a conventional third generation CT scanner with the scanner's X-ray source irradiating an axial slice of a patient with a metal insert, in the region of the thorax, at two different subfan angles.

FIG. 1 shows a schematic of elements of a third generation CT scanner 20 comprising an X-ray source 22, irradiating a thin axial slice 24, of the thorax region of a patient at two different subfan angles $\theta_1$ and $\theta_2$. Shown in the thorax is a cross section of a diagrammatic vertebra 26, and a metal insert 28. The drawing is not to scale and slice 24 is indicative and not realistic.

X-ray source 22 is collimated so that X-rays emanating from it are confined within a thin fan beam 30. On the opposite side of the slice to X-ray source 22, an array 32, of N narrow aperture X-ray detectors 34, labeled $D_1$ through $D_N$, are aligned facing X-ray source 22. Each narrow aperture X-ray detector 34 defines a narrow tubule 36, of X-rays in beam 30 along the line projected from X-ray source 22 to the X-ray detector 34. The cross section of a tubule 36 is substantially equal to the aperture area of the X-ray detector 34 which defines it. Each X-ray detector 34 thus measures the intensity of X-rays that reach it after traversing material in slice 24 within the tubule 36 which it defines. Signals generated by each detector 34 are measures of the attenuation of the X-ray beam resulting from the composition and density distribution of the material of slice 24 in the particular tubule 36 which each detector 34 defines.

Figure 2:
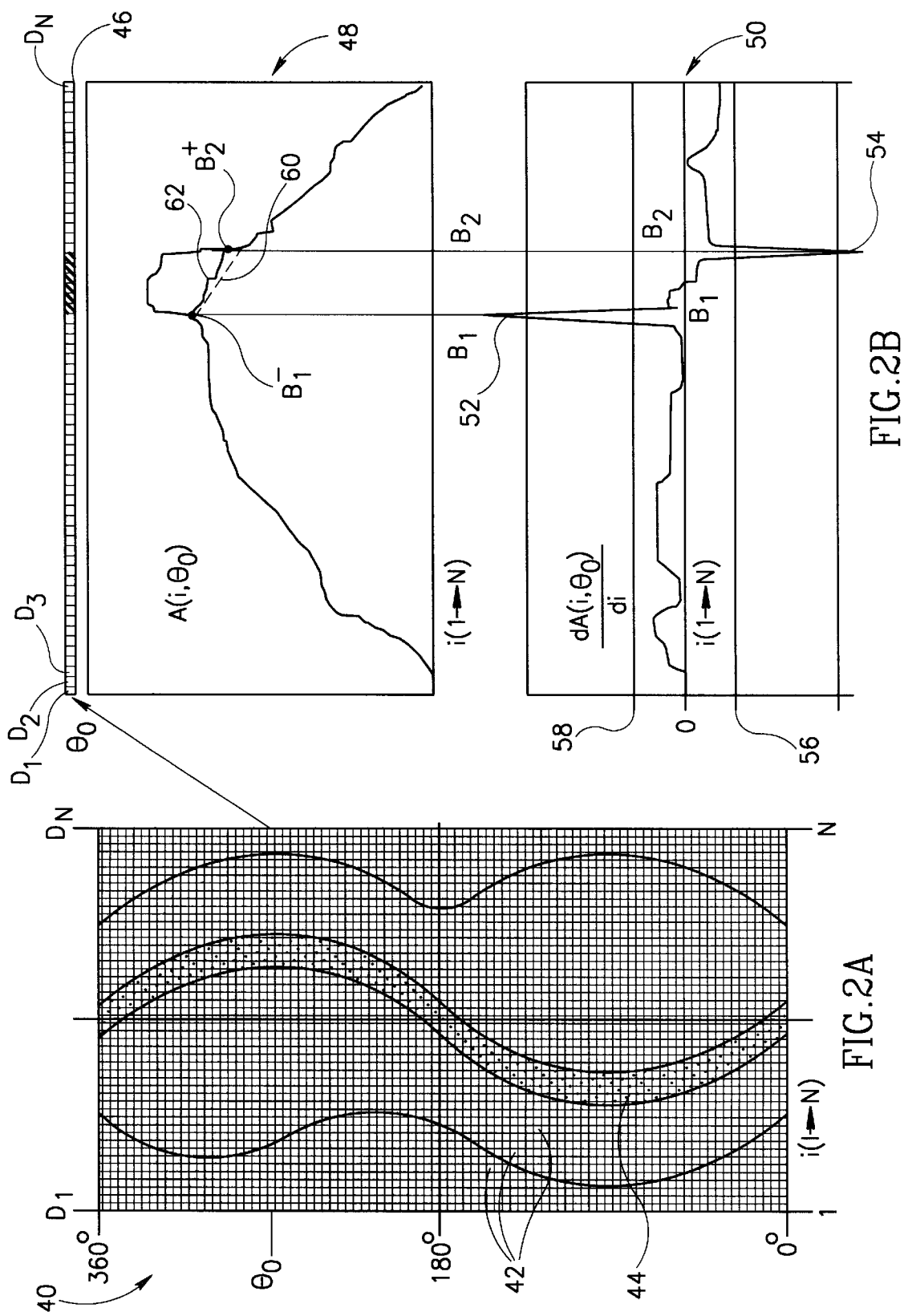
FIGS. 2A and 2B respectively show a sinogram of simulated attenuation data for the slice irradiated in FIG. 1 and details of the data and processed data for a particular view with adjustments in accordance with a preferred embodiment of the present invention.

FIG. 2A shows a sinogram 40, of simulated attenuation measurements acquired for a projection set, spanning view angles 0–360 degrees, for slice 24 shown in FIG. 1. Sinogram 40 is a visual presentation of the attenuation measurements comprising a rectangular array of pixels 42 where the abscissa of the array represents the identifying subscript i of the detector at which an attenuation measurement is made and the ordinate is the view angle at which the measurement is made. A shade of gray which fills a particular pixel 42 at coordinates i,$\theta$ in sinogram 40 represents a magnitude of attenuation measured by a detector $D_i$ at a view angle $\theta$. If the attenuation measured by detector $D_i$, at view angle $\theta$ is $A(i,\theta)$, then the shade of gray of pixel i,$\theta$, represents the magnitude of $A(i,\theta)$.

Pixels representing relatively large attenuation measurements resulting from metal insert 28 are highly contrasted against the background intensity of sinogram 40. The locus of these pixels in sinogram 40 approximates a band 44, in the shape of a sine curve, whose width at ordinate $\theta$ represents substantially the projected width of metal insert 28 at view angle $\theta$.

FIG. 2B shows an expanded view 46, of the row of pixels 42 from sinogram 40 that represents attenuation measurement $A(i,\theta_0)$, at a view angle $\theta_0$. Also shown are graphs 48 and 50, which graph respectively, the measured attenuation $A(i,\theta_0)$ and the derivative of the measured attenuation $dA(i,\theta_0)/di$, for the row at $\theta_0$ as a function of pixel number i, in the row. The width of metal insert 28, which is represented by the width of band 44 in sinogram 40 is represented in both graphs 48 and 50. However, the width is particularly well defined in graph 50 by two very large peaks 52 and 54 which protrude significantly above the background. By setting appropriate threshold values 56 and 58 for the derivative $dA(i,\theta_0)/di$ of the attenuation values, in accordance with a preferred embodiment of the present invention, peaks 52 and 54 are relatively easily located as a function of i, preferably automatically by an appropriate computer routine.

A metal insert in a view angle has one boundary at a first value of i where $dA(i,\theta_0)/di$ is positive and a second boundary at a larger value of i where $dA(i,\theta_0)/di$ is negative. Therefore, in locating the boundaries of metal insert 28 by locating peaks 52 and 54, preferably the computer routine searches the data as a function of increasing i for two consecutive peaks of opposite sign, the first positive and the second negative, which have magnitudes exceeding the threshold. The first peak identified, peak 52, identifies the first boundary of metal insert 28 at position $B_1$ and the second peak identified, peak 54, identifies the second boundary at position B2.

In some preferred embodiments of the present invention, alternatively or additionally, the second derivative of $A(i, \theta_0)$, $d^2A(i,\theta_0)/d^2i$ is used in locating $B_1$ and $B_2$. At both $B_1$ and $B_2$, $d^2A(i,\theta_0)/d^2i$ has a very specific signature. At $B_1$, $d^2A(i,\theta_0)/d^2i$ is zero and it has a large positive peak just before $B_1$ and a large negative peak just following $B_1$. At $B_2$, $d^2A(i,\theta_0)/d^2i$ is also zero and has on either side of $B_2$ a large peak in its value. But at $B_2$ the sign of the peaks is reversed and it has a large negative peak just before $B_2$ and a large positive peak just following $B_2$.

In accordance with a preferred embodiment of the present invention, measured values of attenuation $A(i,\theta_0)$, for which $B_1 < i < B_2$, are replaced with adjusted values in order to improve the CT image of slice 24. The adjusted values are calculated from an estimate of a contribution $C(i,\theta_0)$, to each attenuation measurement $A(i,\theta_0)$, in the range $B_1 < i < B_2$ that arises from metal insert 28. $C(i,\theta_0)$ is preferably calculated from a linear interpolation line 60. Preferably line 60 is the line between measured attenuation values $A(B_1^-,\theta_0)$ and $A(B_2^+,\theta_0)$, at points $B_1^-$ and $B_2^+$, just outside of boundaries $B_1$ and $B_2$ of metal insert 28. Alternatively, line 60 is preferably the line between average values of $A(i,\theta_0)$ at points $B_1$ and $B_2$, where the averages are taken over points in small areas located at $B_1^-$ and $B_2^+$ respectively. If the values of linear interpolation line 60 at points i are noted as $L(i,\theta_0)$, then, preferably, $C(i,\theta_0) = A(i,\theta_0) - L(i,\theta_0)$. The adjusted value for each point i in the range $B_1 < i < B_2$ which replaces $A(i,\theta_0)$ is preferably $[A(i,\theta_0) - fC(i,\theta_0)]$, where f is a fraction. By choosing fractional values for f in accordance with a preferred embodiment of the present invention, data from metal insert 28 is not removed from the projection set of slice 24 but only moderated (f=1 substantially removes the data from the projection set). In this way, a method in accordance with the present invention, images metal insert 28 in a CT image of slice 24 ( albeit not at it's correct CT number) while simultaneously reducing or removing artifacts that metal insert 28 causes in the CT image.

The value of f preferably depends upon the material of the metal insert and the CT number of the material as determined from the attenuation data or as known a priori.

For most metals f is preferably greater than 0.5. For metal inserts made from iron, f is preferably greater than 0.7. Preferably, f is in the range from 0.7 to 0.8. Most preferably, f is substantially equal to 0.75.

For metal inserts made from heavier metals such as mercury, gold or platinum, preferably, f is greater than 0.8. More preferably, f is greater than 0.9. Most preferably, f is in the range from 0.93 to 0.99. Preferably, f is substantially equal to 0.95.

Values for f that are less than 0.5 can also improve the quality of an image with a metal insert. Generally, as f increases, artifacts caused by a metal insert fade and the edges of the insert and the position of the insert with respect to nearby body tissue are more clearly imaged. The intensity with which the metal insert is imaged also decreases. At some value for f, an optimum balance is achieved between the artifacts and the intensity with which the metal insert is imaged.

Where the adjustments to data in accordance with a preferred embodiment of the present invention are performed automatically by computer it is possible to change values of f and observe how the changes affect the CT image constructed from the adjusted data. In this way it is possible to visually optimize a choice for f. Adjusted values for the data between $B_1$ and $B_2$ for f=0.75 is shown as line 62 in graph 48.

For view angles where one or more metal inserts in a patient shadow each other and/or dense biological tissue or other medium CT number objects (e.g. structural parts of a bed on which a patient lies), it may become difficult to accurately identify metal insert borders and calculate adjusted attenuation values using data adjustment procedures described above. In these cases it is preferable to recognize that a problem situation exists and modify the way in which attenuation data is adjusted by incorporating information available from views adjacent to or near to the problem view where the problem situation does not exist. Preferably this is done automatically by appropriate routines in a computer program.

In a preferred embodiment of the present invention, recognition that a problem situation exists at a particular view angle is accomplished by establishing a set of constraints that must be satisfied by the data in the view. By definition, when the constraints are not satisfied, a problem situation exists at the particular view angle and attenuation data is adjusted by using information from adjacent non-problematic views.

Two problems generally arise: 1) the widths of metal inserts in a problem view are not consistent with the widths of the inserts measured in other views; or 2) the estimated value for the contribution to attenuation measurements from metal inserts, $C(i,\theta)$, at the problem view are not consistent with the estimations in other views.

The widths of metal inserts should change smoothly from view to view. When this does not happen in the transition from one view to an adjacent view, data is flawed in the view where the width of a metal insert or metal inserts exhibit large abrupt changes. For the problematic view the positions of boundaries of metal inserts exhibiting large abrupt changes are preferably estimated by interpolation from the positions of boundaries of these metal inserts in adjacent or nearby non problematic views.

As for the contributions to the attenuation from metal inserts, the total attenuation from a metal insert at a view angle, $$\sum_{i=1}^{N} C(i, \theta)$$

should independent of $\theta$. Therefore the sum of the total attenuation from all metal inserts at a view angle should also be independent of view angle. When the total attenuation from all metal inserts at a particular view is anomalous, the attenuation resulting from each individual metal insert in the view is preferably checked for consistency with data from other views. An inconsistent value for the attenuation $C(i,\theta)$, from a particular metal insert is generally the result of an erroneous estimation of the background attenuation $L(i,\theta)$, for the region of the metal insert. For the insert with the anomalous estimate of attenuation $C(i,\theta)$, the function $L(i,\theta)$ is preferably iteratively varied until $C(i,\theta)$ for the metal insert is consistent with data from the other views.

A constraint set in accordance with a preferred embodiment of the present invention, applicable to the data of a projection set for a slice having at least one metal insert, preferably requires: 1) the width of a metal insert in any view should not differ by more than two standard deviations from the width of the metal insert averaged over all the views; 2) from view to view the sum of the widths of all metal inserts should change smoothly; 3) the assessed contribution to attenuation measurements from each metal insert in a view, and the sum of the assessed contributions to attenuation measurements from all metal inserts in a view, for any particular view, should be within two standard deviations of their averages taken over all views of the projection set.

Figure 3:
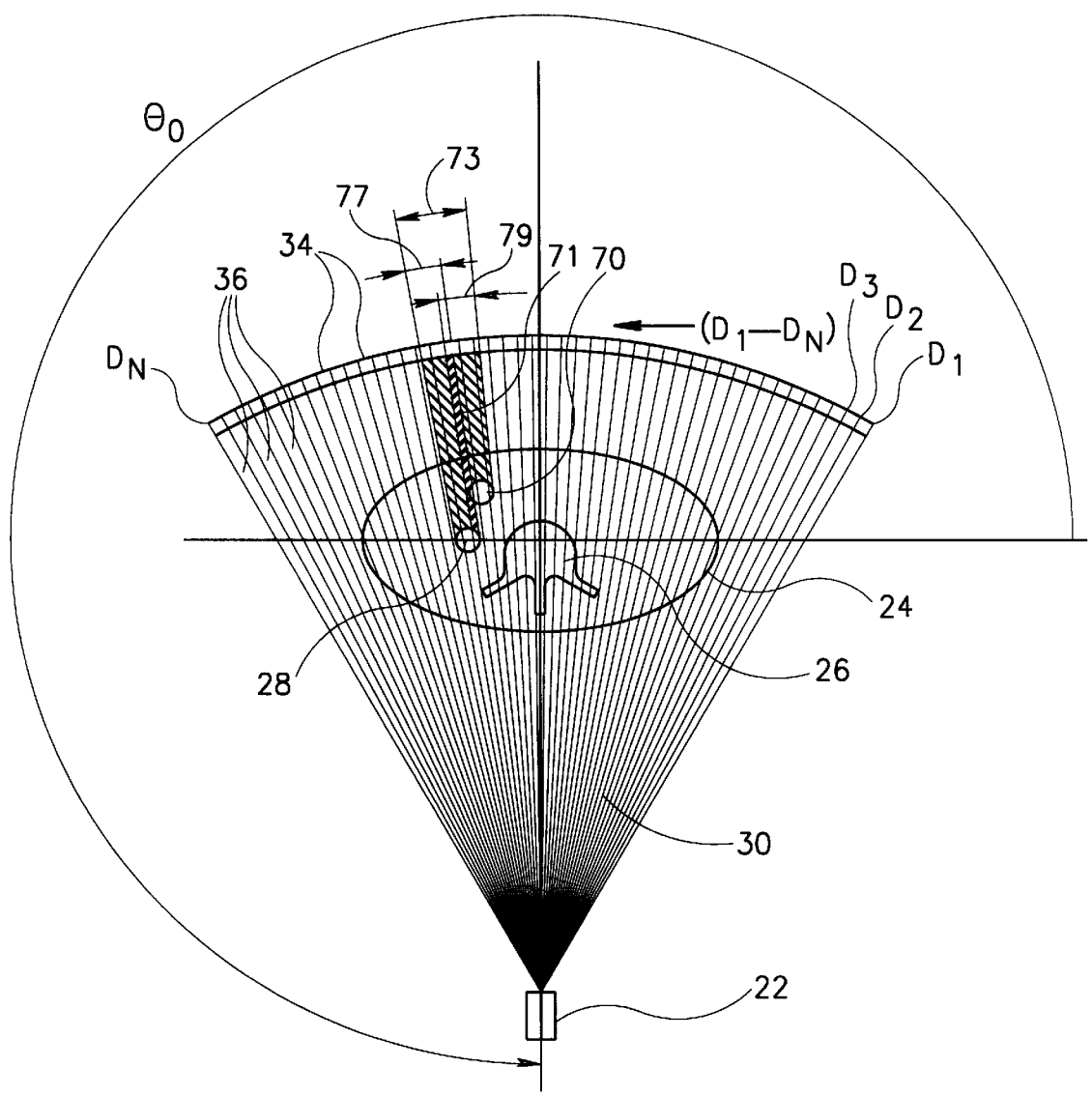
FIG. 3 shows a slice similar to that of FIG. 1 with an additional metal insert for radiation at a subfan angle at which two inserts shadow each other.

FIG. 3 illustrates a situation where constraint 3 noted above might not be satisfied for a view in a projection set of a slice. FIG. 3 shows slice 24 of FIG. 1 with a second metal insert 70, at the same view angle $\theta_0$ for which $A(i,\theta_0)$ and $dA(i,\theta_0)/di$ are graphed in FIGS. 2A and 2B respectively.

At and near to this view angle, metal insert 70 and metal insert 28 shadow an unbroken continuous region 73 of fan beam 30 and shadow each other near to their edges in an overlap region 71. Region 73 is much wider than regions 77 and 79, which are the regions shadowed individually by metal inserts 28 and 70 respectively.

As the breadth across which a linear interpolation $L(i,\theta)$, of background is made increases, the less likely will $L(i,\theta_0)$, accurately represent the background. Therefore, the linear interpolation $L(i,\theta)$, of the background in region 73 is liable to be significantly less representative of the real background than linear interpolations of backgrounds over smaller regions like 77 and 79.

As a result, assessed contributions to attenuation measurements from each of metal inserts 28 and 70 in view $\theta_0$ (i.e. $\Sigma[C(i,\theta_0)=A(i,\theta_0)-L(i,\theta_0)]$ where the sum is taken over values of i shadowed by inserts 28 and 70) might well differ by more than two standard deviations from their respective assessed attenuation contributions per view, averaged over all views of the projection set. Constraint 3 of the constraint set would not be satisfied. The attenuation adjustment procedure would preferably be flagged to adjust $L(i,\theta)$ so that the attenuation contributions calculated for metal inserts 28 and 70 are consistent with data from other views.

The adjustment is preferably made by an iterative trial and error procedure comprising multiplying $L(i,\theta)$ by a factor close to one to get a new $L(i,\theta)$, and testing to see if the calculated attenuation contributions using the new $L(i,\theta)$ satisfy constraint 3. If they do not another multiplicative factor is tried. This procedure is repeated until satisfactory results are obtained.

Figure 4:
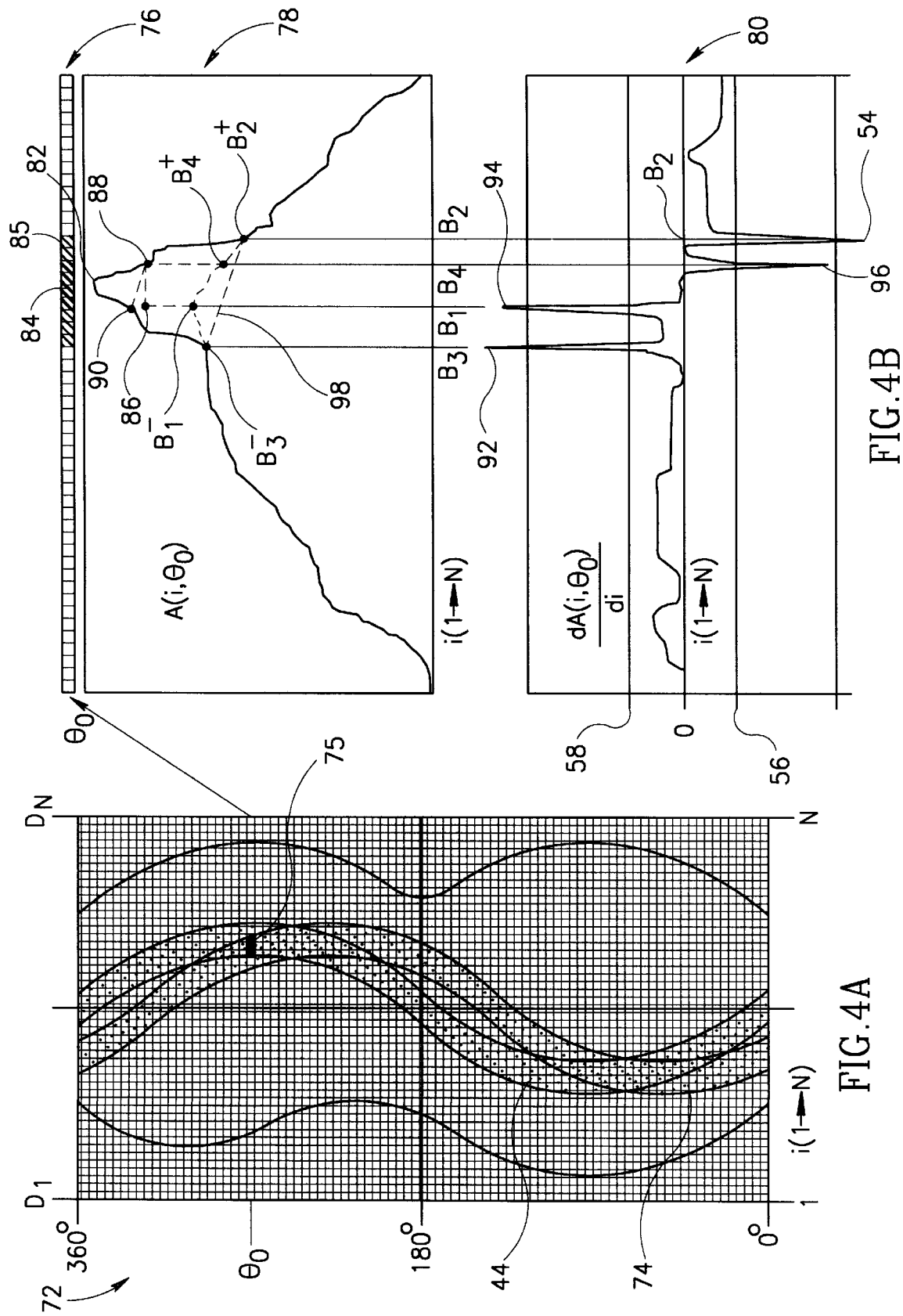
FIGS. 4A and 4B respectively show a sinogram of simulated attenuation data for the slice shown in FIG. 3 and details of the data and processed data for a view angle shown in FIG. 3.

A sinogram and graphs for simulated processed data resulting from the situation shown in FIG. 3 is shown in FIG. 4A and FIG. 4B respectively.

FIG. 4A shows a sinogram 72, of slice 24 in which for some views metal inserts 28 and 70 shadow each other. Sinogram 72 shows, in addition to band 44 in sinogram 40 from metal insert 28, a sine shaped band 74, which is the locus of pixels affected by metal insert 70. A band overlap region 75 at ordinate $\theta_0$ corresponds to overlap region 71 of fan beam 30 shown in FIG. 3.

FIG. 4B shows an expanded view 76, of the row of pixels from sinogram 72 that represents attenuation measurements $A(i,\theta_0)$, at view angle $\theta_0$, and graphs 78 and 80, of $A(i,\theta_0)$ and $dA(i,\theta_0)/di$ respectively. Band overlap region 75 in sinogram 72 corresponds to a narrow peak 82 in graph 78 and is represented by the most darkened pixels 84 in expanded view 76.

Graph 78 is similar to graph 48 with the addition of changes due to metal insert 70. Metal inserts 70 and 28 affect the attenuation values in the range from $B_3^-$ to $B_2^+$ (the superscripts – and + indicate points just to the left of $B_3$ and just to the right of $B_2$ respectively). In this region, in the absence of metal insert 70 the graph would follow the dotted lines connecting points $B_3^- \rightarrow B_1^- \rightarrow 86 \rightarrow 88$ and then continue along the solid line to $B_2^+$. Similarly, in the absence of metal insert 28 the graph would follow the solid curve from B3– to point 90 and from there the dotted curve connecting points $90 \rightarrow 88 \rightarrow B_4^+ \rightarrow B_2^+$. The real background in the region shadowed by metal inserts 28 and 70, which would be the attenuation measurements in the absence of the inserts, is shown by the curve connecting points $B_3^- \rightarrow B_1^-$ $B_4^+ \rightarrow B_2^+$.

The boundary points of the regions affected by metal inserts 28 and 70 are located from the derivative $dA(i,\theta_0)/di$ shown in graph 80. The right hand boundary of the region of graph 78 affected by metal inserts 28 and 70 is the boundary of metal insert 28, which is at the same point, B2, located from peak 54 that appears in graph 50. The left hand boundary of the affected region is a boundary of metal insert 70 at $B_3$ located from peak 92. The boundaries of band overlap region 75, $B_1$ and $B_4$, corresponding to the width of peak 82 in graph 78 are indicated by peaks 94 and 96 in $dA(i,\theta_0)/di$. Peaks 94 and 96 are smaller than peaks 92 and 54 because of beam hardening, which causes the attenuation in the overlap region to be less than the sum of the attenuations measured for each of metal inserts 28 and 70 in the absence of the other. Beam hardening also tends to broaden peaks 94 and 96.

The boundaries of metal inserts 28 and 70 are preferably located in two passes through the projection data, preferably searching for pairs of oppositely signed peaks. In a pass through the data, in the direction from $i=1 \rightarrow N$, a pair of peaks is preferably searched for, where the first peak is positive and the second peak is negative. This pass identifies peaks 92 and 96. In a second pass through the data, in the opposite direction, from $i=N \rightarrow 1$, a pair of peaks is preferably searched for where the first peak is negative and the second peak positive. This pass identifies peaks 54 and 94.

The four peaks are preferably paired so that they are consistent with the widths of inserts in the other views. For example, if a narrow metal insert is shadowed by a wide one, peak 94 would be paired with peak 96, and peak 92 with peak 54. If two metal inserts are overlapping at their edges, peak 94 would be paired with peak 54, and peak 92 with peak 96. In the case shown in FIGS. 3 and 4, metal inserts 28 and 70 shadow each other at their edges, and peak 94 is paired with peak 54, and peak 92 with peak 96.

Background interpolation is preferably performed between the two peaks 92 and 54 corresponding to the widest metal insert width in the data. The background data is therefore preferably estimated by straight line 98 between points B2+ and B3– in graph 78. The values along line 98 differ significantly from the real background represented by the values along the curve connecting points $B_3^- \rightarrow B_1^-$ $\rightarrow B_4^+ \rightarrow B_2^+$. If the sum of the values for $C(i,\theta_0)$, between $B_3^-$ and $B_2^+$ calculated using values from line 98 differs by more than two standard deviations from the total average attenuation resulting from metal inserts 28 and 70 taken over all views of the projection set for slice 24, then constraint 3 is not satisfied. In this case line 98 is preferably raised or lowered by small amounts in a trial and error iteration procedure, until the calculated attenuation estimates for metal inserts 28 and 70 are consistent with data from the other views in the projection set.

Figure 5:
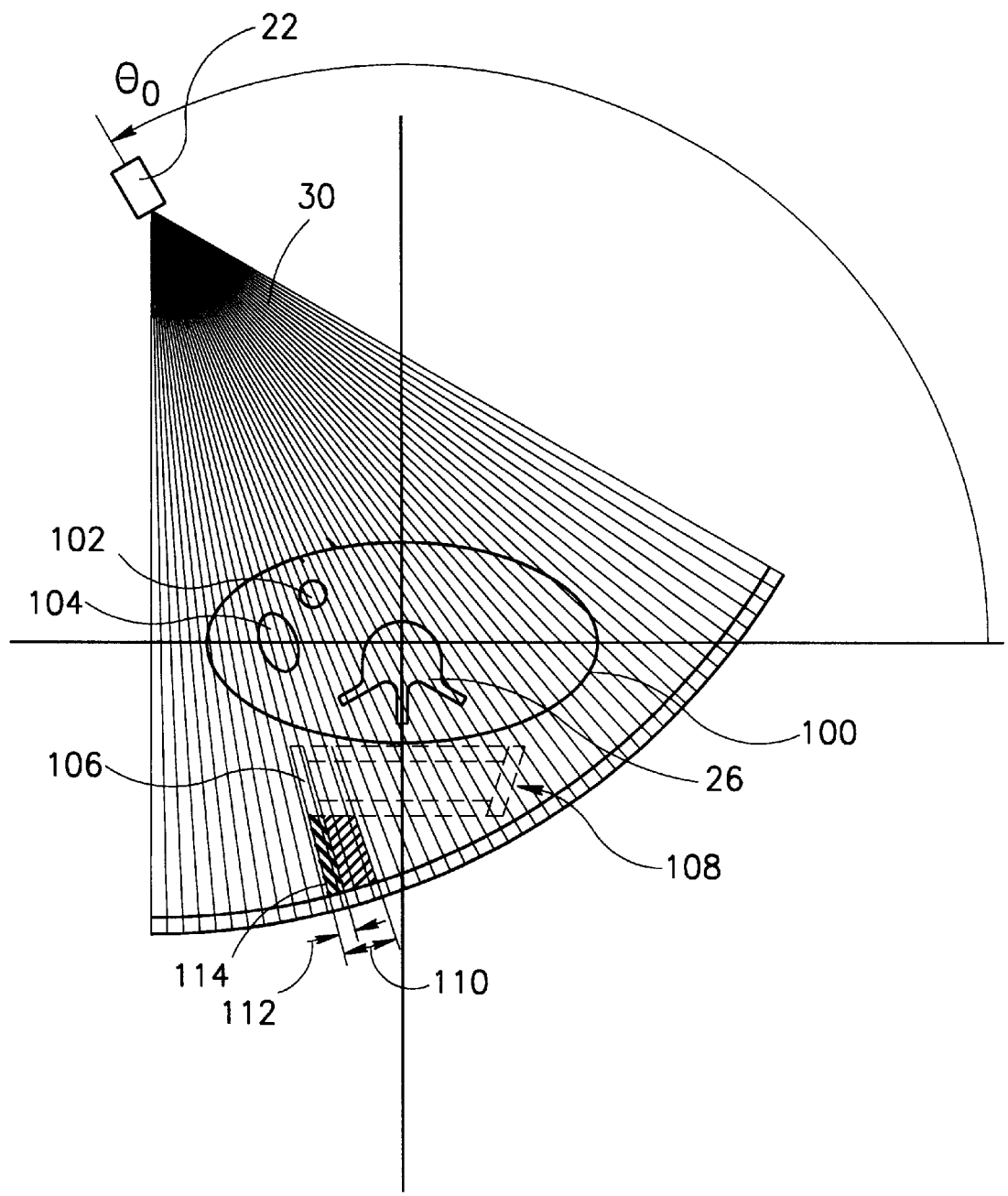
FIG. 5 shows a slice similar to that of FIGS. 1 and 3 showing bone tissue which is shadowed by a part of a bed on which a patient lies while being scanned.

FIG. 5 is a schematic illustration of a situation where constraints 1 and 2 are not satisfied. Shown in FIG. 5 is a schematic slice 100, of the thorax region of a patient undergoing a CT scan. Slice 100 has a vertebra 26, bone tissue 104 and a metal insert 102 which are shown diagrammatically in cross section. Also shown in FIG. 5 is a structural part 108 of a bed (not shown) on which the patient is lying. Structural part 108 comprises a part 106 which shadows bone tissue 104 at subfan angle $\theta_1$ of fan beam 30. Bone tissue 104 and part 106 shadow fan beam 30 in regions 110 and 112 respectively. Region 112 is contained in region 110 and the two regions have a common boundary 114.

FIG. 6A shows a sinogram 120 of slice 100 shown in FIG. 5 comprising pixel bands 122, 124 and 126 which are the bands of pixels with emphasized intensity resulting from metal insert 102, bone tissue 104, and part 106 respectively. Common boundary 114 shown in FIG. 5 appears in sinogram 120 at a point $B_{10}$ of a view angle $\theta_0$ where bands 124 and 126 from bone tissue 104 and part 106 respectively, have substantially coincident edges.

FIG. 6B shows an expanded view 130 of the row of pixels from sinogram 120 at view angle $\theta_0$, and graphs 132 and 134, of attenuation measurements $A(i,\theta_0)$ and $dA(i,\theta_0)/di$ respectively. In graph 134, lines 136 and 138, represent the threshold values that a peak in the value of $dA(i,\theta_0)/di$ must exceed in order for a metal insert boundary to be identified as having caused the peak.

In graph 134 three peaks 140, 142 and 144 appear in the value of $dA(i,\theta_0)/di$. Peak 140 corresponds to the coincident boundaries of bone tissue 104 and part 106 at B10, and peaks 142 and 144 correspond to the left and right boundaries of metal insert 102 at B11, and B12 respectively. A negative peak in $dA(i,\theta_0)/di$ exceeding threshold 136 in a region 146, of graph 134, indicating a right hand boundary for part 106 is not evident. The peak does not occur because bone material 104 shadows and extends beyond the right hand boundary of part 106 and has a sufficiently high CT number so that the derivative, $dA(i,\theta_0)/di$, is moderated and reduced in region 146. A peak that might have indicated a right hand boundary for part 106 in region 146 is blurred to the point where it is not identifiable.

In accordance with a preferred embodiment of the present invention, a computer routine preferably identifies metal insert boundaries by searching for a large positive peak followed by a large negative peak in $dA(i,\theta_0)/di$ as it searches the data in the direction of increasing i and then a large negative peak followed by a large positive peak in $dA(i,\theta_0)/di$ as it searches the data in the direction of decreasing i. In the search in the direction of increasing i the program identifies a single insert at view angle $\theta_0$ with boundaries located at the positions of peaks 140 and 144. The procedure does not indicate the presence of metal insert 102 as distinct from part 106. In the search in the direction of decreasing i, a single insert is again identified, but this time with boundaries at peaks 144 and 142.

The boundaries and widths of the single insert identified in each of the data searches are inconsistent with each other. In addition, the width of the insert determined from the search in the direction of increasing i differs by more than two standard deviations from the width of the only metal insert that actually is present in slice 100, metal insert 102. Constraints 1 and 2 are thus not satisfied. The attenuation procedure is preferably flagged to the existence of a problem at view angle $\theta_0$ and preferably checks the data to see which of the boundaries identified by peaks 140, 142 and 144, at view angle $\theta_0$, and which pairing of these boundaries, are consistent with boundaries at other views angles. Boundaries that are inconsistent are preferably discarded and replaced by boundaries calculated by interpolation from boundaries at view angles on either side of view angle $\theta_0$. For the case shown in FIGS. 5, 6A and 6B boundary 140 would be discarded and the pair of boundaries 142 and 144 would be kept.

It should be realized that a priori knowledge and other constraints and sets of constraints, other than those mentioned, can be used to define triggers for switching data adjustment procedures in an attenuation data adjustment method, in accordance with a preferred embodiment of the present invention, and such possibilities will occur to persons of the art. It is also noted that other procedures, besides linear interpolation, can be used to estimate values for adjusting attenuation data in a particular view from data in views adjacent to or near to the particular view when a constraint is not satisfied, and such procedures will occur to persons of the art. Furthermore, it should be realized that adjustments to attenuation data acquired for a slice of a subject, in accordance with a preferred embodiment of the present invention, do not require that the attenuation data be processed and rebinned into views. The adjustments can be applied to attenuation data that is not rebinned and processed into views prior to being used to construct an image of the slice.

The detailed description is provided by way of example and is not meant to limit the scope of the invention which is limited only by the following claims:

What is claimed is:

1. A method for locating boundaries of metal inserts in an array of attenuation data of a set of CT X-ray attenuation data comprising a plurality of arrays of attenuation data, wherein each array of attenuation data represents attenuation data acquired for a plurality of substantially contiguous paths through a slice of a subject, comprising:
   (a) evaluating the derivative of the attenuation data with respect to a position coordinate of the array of attenuation data;
   (b) setting a derivative threshold;
   (c) identifying positive and negative boundary peaks as positive and negative peaks in the derivative respectively that have an absolute value greater than the derivative threshold;
   (d) determining the positions of the positive and negative boundary peaks; and
   (e) determining the position of boundaries of metal inserts in the array of attenuation data to be positions of positive and negative boundary peaks.

2. A method in accordance with claim 1 wherein determining the positions of positive and negative boundary peaks comprises:
   (a) evaluating the second derivative of the attenuation data with respect to the position coordinate of the array of attenuation data;
   (b) setting a second derivative threshold;
   (c) setting a second derivative maximum width;
   (d) identifying positive second derivative peak pairs as a positive peak in the second derivative followed by a negative peak, wherein the separation of the positions of the two peaks is less than the second derivative maximum width and wherein the magnitude of both peaks is greater than the second derivative threshold;
   (e) identifying negative second derivative peak pairs as a negative peak in the second derivative followed by a positive peak, wherein the separation of the positions of the two peaks is less than the second derivative maximum width and wherein the magnitude of both peaks is greater than the second derivative threshold;
   (f) determining the position of each positive and negative second derivative peak pair as the position of the point between the two peaks at which the second derivative is zero; and
   (g) determining the positions of positive boundary peaks as the positions of positive second derivative peak pairs and the positions of negative boundary peaks as the positions of negative second derivative peak pairs.

3. A method according to claim 1 or claim 2 for determining the extent of each of at least one metal insert in an array of attenuation data of CT attenuation data comprising:
   (a) defining boundary peak pairs, wherein a boundary peak pair comprises a positive boundary peak and a negative boundary peak chosen from the identified boundary peaks and wherein the positive boundary peak has a value for the position coordinate which is less than the value for the position coordinate of the negative boundary peak; and
   (b) determining the extent of each of the at least one metal insert in the array of attenuation data to be a region between the positions of the boundary peaks in a boundary peak pair.

4. A method according to claim 3 comprising requiring that the determined extents of each of the at least one metal insert satisfy at least one constraint of a constraint set.

5. A method according to claim 4 comprising determining the extent of metal inserts of the at least one metal insert in an array of attenuation data where a constraint is not satisfied, by interpolation from data available in arrays of attenuation data adjacent to or near to the array of attenuation data where a constraint is not satisfied.

6. A method according to claim 5 wherein the constraint set comprises a constraint that the absolute difference between the determined extent of each of the at least one metal insert in any array of attenuation data of the set of CT X-ray attenuation data, and its average width, be less than two standard deviations of its average width, where the average width is the width of the insert averaged over all views.

7. A method according to claim 6 wherein the constraint set comprises a constraint that the sum of the determined extents of all of the at least one metal insert, changes smoothly between adjacent arrays of attenuation data of the set of CT X-ray attenuation data.

8. A method according to claim 3 wherein defining boundary peak pairs comprises:
   (a) choosing the positive and negative boundary peaks of a boundary peak pair so that there is no negative boundary peak between them; and
   (b) choosing positive boundary peaks for boundary peak pairs so that, for a positive boundary peak of a boundary peak pair there is no positive boundary peak having a smaller value for the position coordinate that is not a positive boundary peak of a different boundary peak pair or that is not bracketed by the positive and negative boundary peaks of a different boundary peak pair.

9. A method according to claim 8 wherein defining boundary peak pairs comprises:

(a) choosing the positive and negative boundary peaks of a boundary peak pair so that there is no positive boundary peak between them; and (b) choosing negative boundary peaks for boundary peak pairs so that, for a negative boundary peak of a boundary peak pair there is no negative boundary peak having a larger value for the position coordinate that is not a negative boundary peak of a different boundary peak pair or that is not bracketed by the positive and negative boundary peaks of a different boundary peak pair.

10. A method for adjusting attenuation data in a set of CT X-ray attenuation data acquired for a slice of a subject having a metal insert comprising:

(a) determining the contribution that the metal insert makes to the magnitude of each attenuation datum in the set of CT X-ray attenuation data;

(b) adjusting each attenuation datum by subtracting from it a fraction less than one of the determined contribution to its magnitude arising from the metal insert.

11. A method according to claim 10 wherein determining the contribution that the metal insert makes to the magnitude of each attenuation datum in the set of CT X-ray attenuation data, comprises requiring that the contribution to each attenuation datum from the metal insert satisfies at least one constraint in a constraint set.

12. A method in accordance with claim 11 wherein the constraint set comprises a constraint that the sum of the calculated contributions to all attenuation data in an array of attenuation data from a metal insert be constant to within two standard deviations of its average taken over all arrays of attenuation data of the set of CT X-ray attenuation data.

13. A method according to claim 11 wherein determining the contribution to an attenuation datum in the set of CT X-ray attenuation data from the metal insert comprises calculating an estimate for the value of the attenuation datum assuming the metal insert is absent, subtracting the estimate from the attenuation datum and setting the contribution to the attenuation datum equal to the results of the subtraction.

14. A method according to claim 13 wherein calculating an estimate for the value of the attenuation datum assuming the metal insert is absent comprises calculating the estimate from data in the array of attenuation data of the set of CT X-ray attenuation data to which the datum belongs that is not affected by the metal insert.

15. A method according to claim 14 wherein data in the array of attenuation data of the set of CT X-ray attenuation data to which the datum belongs that is not affected by the metal insert is attenuation data at positions in the array of attenuation data that are adjacent to and outside of the extent of the metal insert in the array of attenuation data.

16. A method according to claim 15 wherein the value of the attenuation datum assuming the metal insert is absent is estimated by linear interpolation between attenuation data or averages of attenuation data at positions in the array of attenuation data that are adjacent to and outside of the extent of the metal insert in the array of attenuation data.

17. A method according to claim 16 wherein determining the contribution that the metal insert makes to the magnitude of each attenuation datum in an array of attenuation data of the set of CT X-ray attenuation data when a constraint of the constraint set is not satisfied comprises iteratively scaling the intercept of the linear interpolation until the constraint is satisfied.

18. A method according to claim 15 wherein determining the extent of the metal insert comprises:

(a) evaluating the derivative of the attenuation data with respect to a position coordinate of the array of attenuation data;

(b) setting a derivative threshold;

(c) identifying positive and negative boundary peaks as positive and negative peaks in the derivative respectively that have an absolute value greater than the derivative threshold;

(d) determining the positions of the positive and negative boundary peaks;

(e) determining the position of boundaries of metal inserts in the array of attenuation data to be positions of positive and negative boundary peaks;

(f) defining boundary peak pairs, wherein a boundary peak pair comprises a positive boundary peak and a negative boundary peak chosen from the identified boundary peaks and wherein the positive boundary peak has a value for the position coordinate which is less than the value for the position coordinate of the negative boundary peak; and (g) determining the extent of each of the at least one metal insert in the array of attenuation data to be a region between the positions of the boundary peaks in a boundary peak pair.

19. A method according to claim 18 wherein determining the positions of positive and negative boundary peaks comprises:

(a) evaluating the second derivative of the attenuation data with respect to the position coordinate of the array of attenuation data;

(b) setting a second derivative threshold;

(c) setting a second derivative maximum width;

(d) identifying positive second derivative peak pairs as a positive peak in the second derivative followed by a negative peak, wherein the separation of the positions of the two peaks is less than the second derivative maximum width and wherein the magnitude of both peaks is greater than the second derivative threshold;

(e) identifying negative second derivative peak pairs as a negative peak in the second derivative followed by a positive peak, wherein the separation of the positions of the two peaks is less than the second derivative maximum width and wherein the magnitude of both peaks is greater than the second derivative threshold;

(f) determining the position of each positive and negative second derivative peak pair as the position of the point between the two peaks at which the second derivative is zero; and (g) determining the positions of positive boundary peaks as the positions of positive second derivative peak pairs and the positions of negative boundary peaks as the positions of negative second derivative peak pairs.

20. A method according to claim 10 wherein determining the contribution that the metal insert makes comprises acquiring knowledge about a CT number for the metal insert and using the acquired knowledge to determine the fraction.

21. A method according to claim 20 wherein acquiring knowledge about a CT number for the metal insert comprises calculating a CT number for the metal insert from the set of CT X-ray attenuation data.

22. A method according to claim 21 wherein the CT number is calculated by a computer program.

23. A method according to claim 10 wherein acquiring knowledge about a CT number comprises acquiring a priori knowledge about the CT number.

24. A method according to claim 10 wherein the fraction is determined by adjusting the fraction until a view reconstructed from the set of CT X-ray attenuation data is optimized.

25. A method according to claim 10 wherein the fraction is greater than 0.5.

26. A method according to claim 20 wherein the fraction is in the range from 0.7 to 0.8 for metal inserts having a CT number in the region of the CT numbers of iron or titanium.

27. A method according to claim 26 wherein the fraction is substantially equal to 0.75.

28. A method according to claim 20 wherein the fraction is greater than 0.8 for metal inserts having a CT numbers in the region of the CT numbers of mercury, gold or platinum.

29. A method according to claim 28 wherein the fraction is 0.95.

30. A method according to claim 1 or claim 10 wherein the set of CT X-ray attenuation data is a projection set.

31. A method according to claim 30 wherein an array of attenuation data is a view.

* * * * *